(12) United States Patent  
Conroy

(10) Patent No.: US 9,979,867 B2  
(45) Date of Patent: May 22, 2018

(54) IMAGING APPARATUS AND RELATED IMAGE ACQUISITION AND COMPARISON SYSTEMS AND METHODS

(76) Inventor: Meghan Conroy, San Francisco, CA (US)

( * ) Notice: Subject to any disclaimer, the term of this patent is extended or adjusted under 35 U.S.C. 154(b) by 493 days.

(21) Appl. No.: 13/817,456

(22) PCT Filed: Aug. 18, 2011

(86) PCT No.: PCT/US2011/048304  
§ 371 (c)(1),  
(2), (4) Date: Feb. 18, 2013

(87) PCT Pub. No.: WO2012/024525  
PCT Pub. Date: Feb. 23, 2012

(65) Prior Publication Data  
US 2013/0242072 A1    Sep. 19, 2013

Related U.S. Application Data

(60) Provisional application No. 61/374,697, filed on Aug. 18, 2010, provisional application No. 61/446,721, filed on Feb. 25, 2011.

(51) Int. Cl.  
G03B 15/05    (2006.01)  
H04N 5/225    (2006.01)  
A61B 5/00    (2006.01)  
G03B 15/07    (2006.01)

(52) U.S. Cl.  
CPC ......... *H04N 5/2254* (2013.01); *A61B 5/0077* (2013.01); *G03B 15/05* (2013.01); *G03B 15/07* (2013.01); *A61B 5/0013* (2013.01); *G03B 2215/0575* (2013.01); *G03B 2215/0582* (2013.01)

(58) Field of Classification Search  
CPC ......... A61B 5/445; A61B 5/442; A61B 5/444; G06K 9/00234  
See application file for complete search history.

(56) References Cited

U.S. PATENT DOCUMENTS

| | | | |
|---|---|---|---|
| 6,488,629 B1 | 12/2002 | Saetre et al. | |
| 8,260,010 B2 * | 9/2012 | Chhibber | A61B 5/442 382/118 |
| 2002/0044682 A1 * | 4/2002 | Weil | G08B 21/043 382/154 |
| 2006/0285730 A1 | 12/2006 | Habets et al. | |
| 2007/0073776 A1 * | 3/2007 | Kalalian | G06F 17/30274 |
| 2008/0031505 A1 | 2/2008 | Barski et al. | |
| 2010/0150311 A1 * | 6/2010 | Takasawa | A61B 6/00 378/98 |
| 2010/0183206 A1 | 7/2010 | Carlsen et al. | |
| 2013/0096392 A1 | 4/2013 | Adams | |

* cited by examiner

*Primary Examiner* — Obafemi Sosanya

(57) ABSTRACT

An imaging apparatus and related image acquisition, storage and analysis systems and methods is disclosed. The imaging apparatus comprises a lighting source configured to reflect light off of a reflector to ensure consistent lighting of an object of interest for purposes of visual imaging and analysis. The related image acquisition, storage and comparison systems and methods allow for the acquisition, storage and comparison of images using software and various computers and other modules configured to perform such functions.

21 Claims, 19 Drawing Sheets

IMAGING APPARATUS AND RELATED IMAGE ACQUISITION AND COMPARISON SYSTEMS AND METHODS

REFERENCE TO PRIORITY APPLICATION

This application claims priority to U.S. Provisional Patent Application No. 61/374,697 filed on Aug. 18, 2010, titled CLINICAL IMAGING APPARATUS AND METHODS, AS WELL AS DIAGNOSTICS BASED THEREON and U.S. Provisional Patent Application No. 61/446,721 filed on Feb. 25, 2011, titled CLINICAL IMAGING APPARATUS AND METHODS, COMPARATIVE ORGANIZATION OF IMAGES, AS WELL AS DIAGNOSTICS BASED THEREON, the entire disclosures of which are incorporated herein by reference.

TECHNICAL FIELD

The present invention relates generally to still and motion imaging and analysis, and more specifically, to devices and methods for uniformly acquiring and analyzing images or videos in a variety of settings.

BACKGROUND

The field of medicine has seen many advancements in diagnostic imaging techniques. For example, imaging technologies such as X-rays, CT scanning, mammography and magnetic resonance imaging allow doctors to view structures within the human body that were not previously viewable other than through invasive means. These non-invasive imaging techniques have been instrumental in improving clinical safety and patient outcomes. However, despite the benefits achieved through use of current non-invasive imaging techniques, such techniques contribute to the rising costs of healthcare and may have long term detrimental effects on patients due to the high levels of radiation used in connection with such techniques. Further, such techniques are not useful in medical arts such as dermatology where external visual imaging (e.g., photos, video) and analysis are the main diagnostic techniques.

External visual imaging techniques have long been an integral part of diagnosing and treating patient ailments. Some medical arts (e.g., dermatology) rely almost exclusively on external visual imaging. For example, skin ailments such as melanoma are often characterized through a doctor's visual analysis of the patient's skin. A doctor treating melanoma is primarily concerned with the size and shape of the melanoma at a given time as well as how the size and shape of the melanoma are changing over time.

External visual imaging techniques are also used in other fields. For example, in the cosmetics industry, research scientists must visually study how make-up, creams (e.g., wrinkle and cellulite treatments), and other products affect the appearance of subjects over a course of treatment using such cosmetic products. Additionally, pharmaceutical researchers involved in clinical trials must visually study certain experimental topical therapeutics to determine the efficacy of such therapeutics on patients suffering from various skin ailments. The results of such visual studies are then used to support regulatory filings with the goal of having such therapeutics approved for sale to consumers.

Since external visual imaging in the medical arts is primarily concerned with how certain structures on the human body are changing over time, both still and motion photography have become vital tools for image acquisition and storage. Such still and motion photography allows doctors and clinical researchers to study images taken at one time with images taken at a later time to assess how a patient's condition is changing as a function of time. However, the use of still and motion photography in the medical arts presents a unique set of challenges.

A primary challenge inherent in the use of still and motion photography is a potential lack of consistency during the acquisition and analysis of images. For example, non-uniform lighting conditions may make image comparison between two different photographs or videos difficult. Another challenge arises during studies when pre-defined image acquisition protocols depend on correct and consistent patient position or posture. Image analysis and comparison is made more difficult when even slight position changes of the camera with respect to the subject occur between two different images. Another challenge involves the photographic equipment itself. Bulky cameras, video cameras and lighting setups are expensive and difficult for medical practitioners (who in most cases are not trained photographers) to use in doctor's offices and other healthcare settings. Such equipment setups are also difficult to deploy and use consistently at multiple investigator sites when clinical trials are being performed. Still other challenges involve the lack of efficient systems and methods to store, retrieve and analyze images for purposes of patient care. Therefore a need exists in the art that addresses the challenges presented by current external visual imaging and analysis techniques.

SUMMARY OF THE INVENTION

The above-described problems are addressed and a technical solution is achieved in the art by the imaging apparatus and related image acquisition and comparison systems and methods described herein. According to an embodiment of the present invention, an imaging apparatus comprises a reflector having an aperture; an image acquisition device comprising a lens, said image acquisition device connected to the reflector; and a light source connected to an inner surface of the reflector and configured to emit light reflecting off of the inner surface of the reflector, then reflecting off of an object of interest, and focused through the aperture and into the lens.

According to an embodiment of the present invention, an imaging apparatus comprises a reflector having an aperture; a mounting plate comprising an aperture, a lower plate connected to an outer surface of the reflector, an upper plate rotatably connected to the lower plate, and a mounting bracket connected to the upper plate, wherein the aperture of the mounting plate aligns with the aperture of the reflector; an image acquisition device comprising a lens, wherein the image acquisition device is removably engaged to the mounting bracket; and a light source connected to an inner surface of the reflector and configured to emit light reflecting off of the inner surface of the reflector, then reflecting off of an object of interest, and focused through the aperture and into the lens.

According to an embodiment of the present invention, method for acquiring and analyzing images of a subject, comprises the steps of providing to a user, via a user interface, instructions for posing a subject according to a protocol; receiving, via an imaging apparatus, a first set of images and a second set of images taken in accordance with the protocol; storing, on a computer readable memory, the first set of images and the second set of images; providing for display, via the user interface, the first set of images and the second set of images for comparison purposes.

BRIEF DESCRIPTION OF THE DRAWINGS

The present invention will be more readily understood from the detailed description of exemplary embodiments presented below considered in conjunction with the attached drawings, of which.

Figure 1:
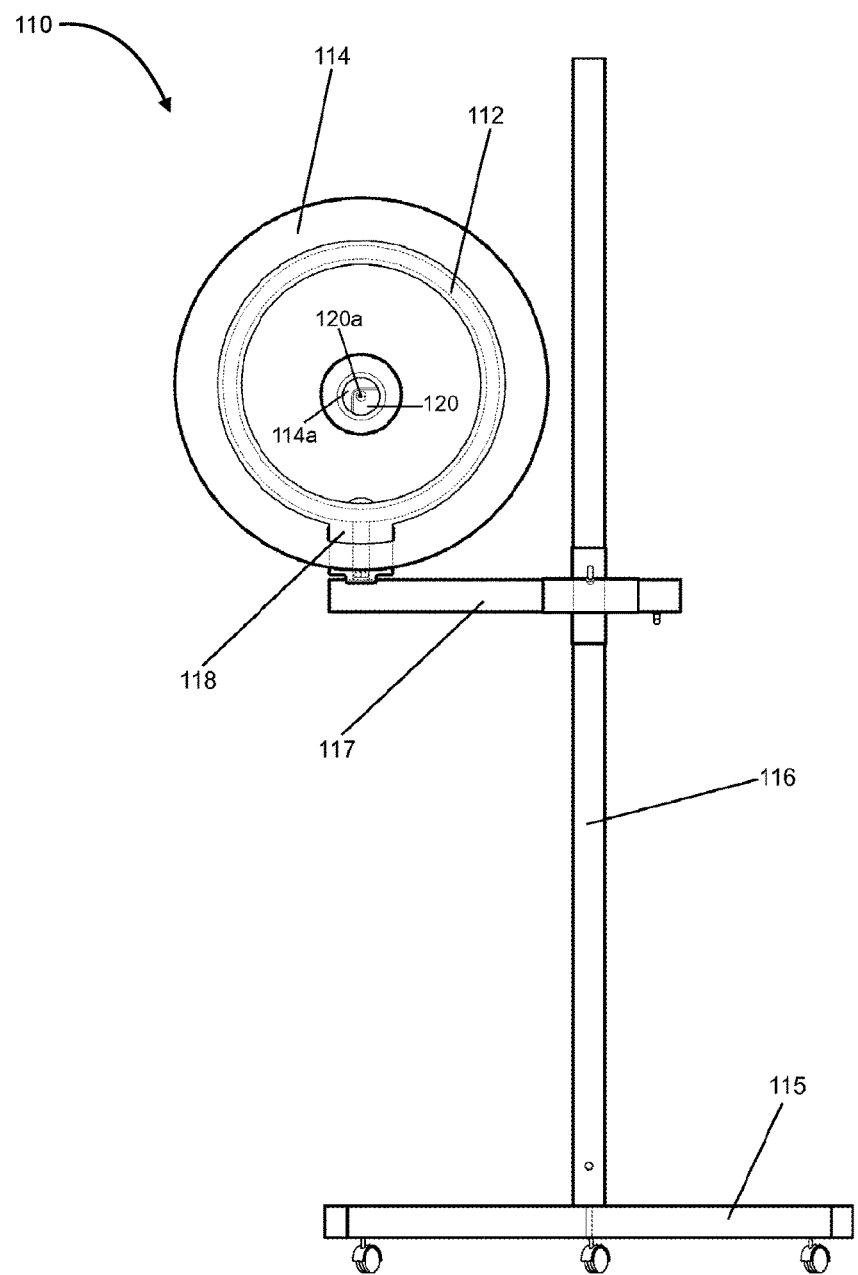
FIG. 1 depicts a front view of an imaging apparatus, according to an embodiment of the present invention.

It is to be understood that the attached drawings are for purposes of illustrating the concepts of the invention and may not be to scale, and are not intended to be limiting in terms of the range of possible shapes and/or proportions. Like reference numerals refer to corresponding parts throughout the several views of the drawings.

DETAILED DESCRIPTION OF THE INVENTION

Embodiments of the present invention relate to an imaging apparatus and related systems and methods for the acquisition, organization and analysis of still and video images. According to an embodiment of the present invention, the apparatus comprises a reflector and a light source connected to the reflector, wherein the light source is configured to generate light so as to reflect off of an inner surface of the reflector. According to an embodiment of the present invention, the related systems and methods for the acquisition, organization and analysis of images comprises the steps of acquiring and/or storing a first set of images of a subject in accord with an imaging protocol on a first date, each of the subject images of the protocol corresponding to one of a predetermined set of subject poses or movements; acquiring and/or storing a second set of images or videos of the subject in accord with the imaging protocol on a second date, each of the subject images of the protocol corresponding to one of the predetermined set of subject poses; and displaying for comparison at least one of the images of the first set of images with at least one of images of the second set of images.

For purposes of this specification, terms are to be given their plain and ordinary meaning in the context in which they arise as understood by those possessing ordinary skill in the art. As used herein, the term "connect" is intended to include, but is not limited to, any suitable means or method to engage, mount, attach, connect, integrally connect, affix, join, adhere, etc. As used herein, the term "communicatively connected" is intended to include any type of connection, whether wired or wireless, in which data may be communicated and also includes a connection between devices and/or programs within a single computer or between devices and/or programs on separate computers. As used herein, the term "computer" is intended to include any data processing device, such as a desktop computer, a laptop computer, a tablet computer, a mainframe computer, a personal digital assistant, a server, or any other device able to process, manage or transmit data, whether implemented with electrical, magnetic, optical, biological components or otherwise. The term "module" is intended to include, but is not limited to, one or more computers configured to execute one or more software programs configured to perform one or more functions, operations, and/or actions.

Referring to FIG. 1, an imaging apparatus 110 according to an embodiment of the present invention includes a light source 112, a reflector 114, a stand 116, and a flash controller 118, configured as shown. The light source 112 provides electromagnetic radiation (e.g., light) at least a portion of which is in the visible spectrum, in a generally ring-like pattern although other shapes and configurations are possible. The light source 112 may be configured to provide light in flashes (e.g., for purposes of still imaging) and/or it can be constructed and operated for continuous lighting for both video imaging and still photography applications. The light source 112 may be connected to an image acquisition device 120, by way of any suitable means including, without limitation, threading on its lens. In alternate embodiments, the light source 112 may be connected directly to the reflector 114 by any suitable means. One having ordinary skill in the art will appreciate the various ways in which the light source 112 may be connected to either the image acquisition device 120 or the reflector 114.

For some applications, the light source 112 may be a "ring-type flash" such as that commercially available in the marketplace for still photography. However, the light source 112 need not be circular in shape but could take on a variety of shapes and sizes depending on the particular application. For example, the light source 112 may comprise a rectangular geometry or other geometries depending on the particular application. According to an embodiment of the present invention, the light source 112 may comprise one or more light emitting diodes (LEDs), fluorescent bulbs, halogen bulbs, xenon bulbs, tungsten bulbs, and/or other point light sources configured in a circular or substantially circular pattern of any suitable diameter. Those sources can be suitable for flash lighting (e.g., xenon bulbs) and/or continuous lighting (e.g., tungsten bulbs, fluorescent bulbs) and, indeed, in some embodiments, the individual sources are suitable for both (e.g., LEDs).

According to an embodiment of the present invention, point sources for the light source 112 are selected to generate light in the spectrum visible to humans; however, lighting in other spectra such as infrared and ultraviolet may also be achieved. One having ordinary skill in the art will appreciate that the number and types of light sources will vary depending on the particular application.

According to an embodiment of the present invention, the light source 112 and, more particularly, the lighting sources of which it is comprised, are powered and fired by the flash controller 118. The flash controller 118 can be a flash control unit of the type used in conventional flash photography (e.g., in applications where the point sources are intended for flash lighting) and/or it can be constructed and operated for continuous lighting, for both video imaging and still photography applications. The type and specific flash controller 118 configuration will be apparent to one having ordinary skill in the art.

The diameter of the light source 112 may be determined based on (i) the lens size of the image acquisition device 120 with which the apparatus 110 is used, and (ii) the diameter of the inner reflective surface of the reflector 114, taking into account the need for uniform lighting of the object of interest (or portion thereof) being photographed or videotaped. Without limiting the generality of the foregoing, an object of interest may include a human subject or specific parts of such subject's body. The same principle described above applies for light sources 112 that are other than those that are circular in shape. Commercially available camera lenses typically run from 0.1" (e.g., for digital cameras) to 5" (e.g., SLRs), although some may fall outside this range. According to an embodiment of the present invention, the diameter of the reflector 114 may be in the range of between 0.5" and 36," although other embodiments may be outside of this range. According to an embodiment of the present invention, the diameter of the light source 112 may be in the range of between 0.5" and 6," although other embodiments may be outside of this range.

One having ordinary skill in the art will appreciate that the number, luminosity, and spectrum of the point sources within the light source 112 may selected so as to illuminate the subject (or portion thereof) as uniformly as possible for imaging purposes. By way of example and not limitation, the light source 112 may have a diameter of about 18" and comprise a fluorescent ring bulb configured to operate as a flash and/or continuous light source.

According to an embodiment of the present invention, the reflector 114 is configured to reflect light from the light source 112 in the direction of the subject (or portion thereof) being photographed or videotaped. In order to uniformly light the object of interest being photographed or videotaped and to prevent large contrast gradients in the resulting image, the light source 112 may be configured so as to generate light backwards (i.e., in a direction away from the object of interest (or portion thereof) being photographed) and, instead, directly into the inner reflective surface of the reflector 114. In this way, any harshness and flaring of the resulting light is reduced thereby resulting in an even and uniform light that makes visual analysis of the resulting images more accurate.

According to an embodiment of the present invention, the reflector 114 is a generally hemispherical or conical reflector of the type commercially available in the marketplace for still or motion photography. The reflector 114 has an opening or aperture 114a formed at the back of the inner surface to allow an unobstructed view between the image acquisition device 120 lens 120a and subject being photographed or videotaped. Generally, the aperture 114a will be centered within the opening of the light source 112. The diameter of the aperture 114a is typically greater than or equal to the diameter of the image acquisition device lens 120a. One having ordinary skill in the art will appreciate that a variety of sizes and shapes of reflectors 114 may be used such as "bowl" or "beauty" reflectors. The reflector 114 can be fashioned from metal, ceramic, canvas, plastic or other suitable materials known in the art for such purpose. According to an embodiment of the present invention, the inner reflective surface of the reflector 114 may be white or silver but one having ordinary skill in the art will appreciate that various colors may be used depending on the particular application.

Figure 7:
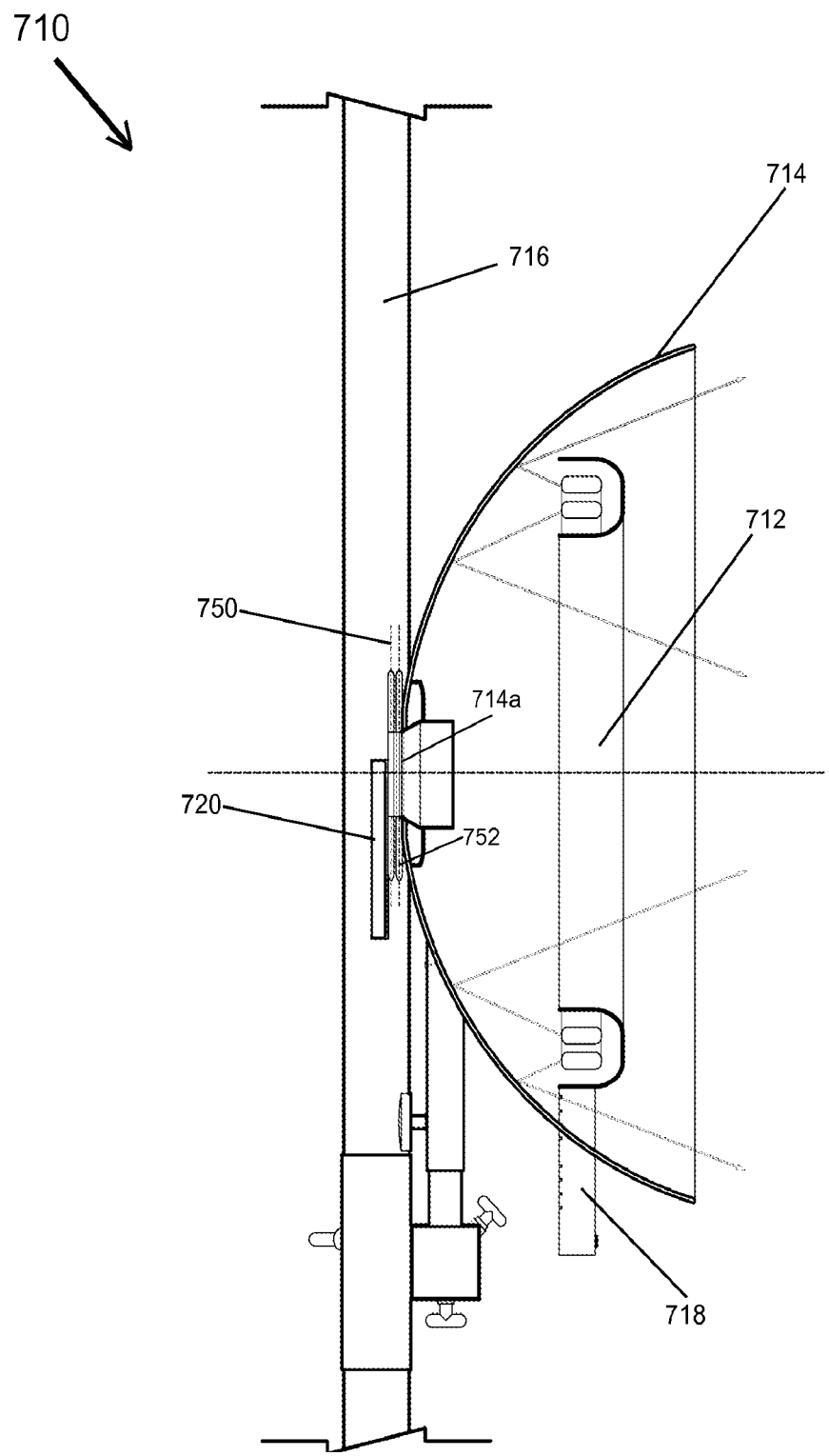
FIG. 7 depicts a side cut-away view of an imaging apparatus, according to an embodiment of the present invention.
Figure 8:
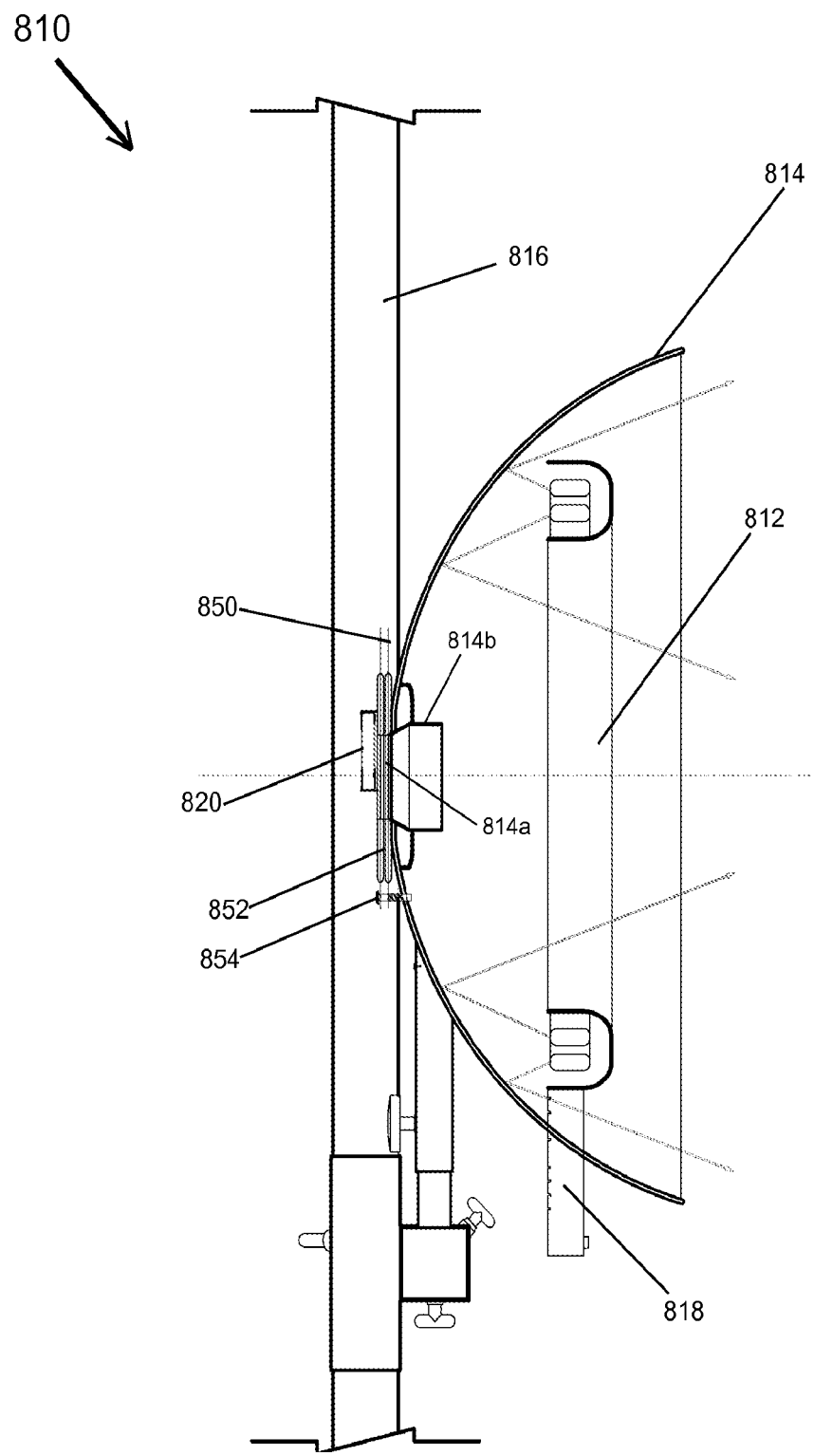
FIG. 8 depicts a side cut-away view of an imaging apparatus, according to an embodiment of the present invention.
Figure 9:
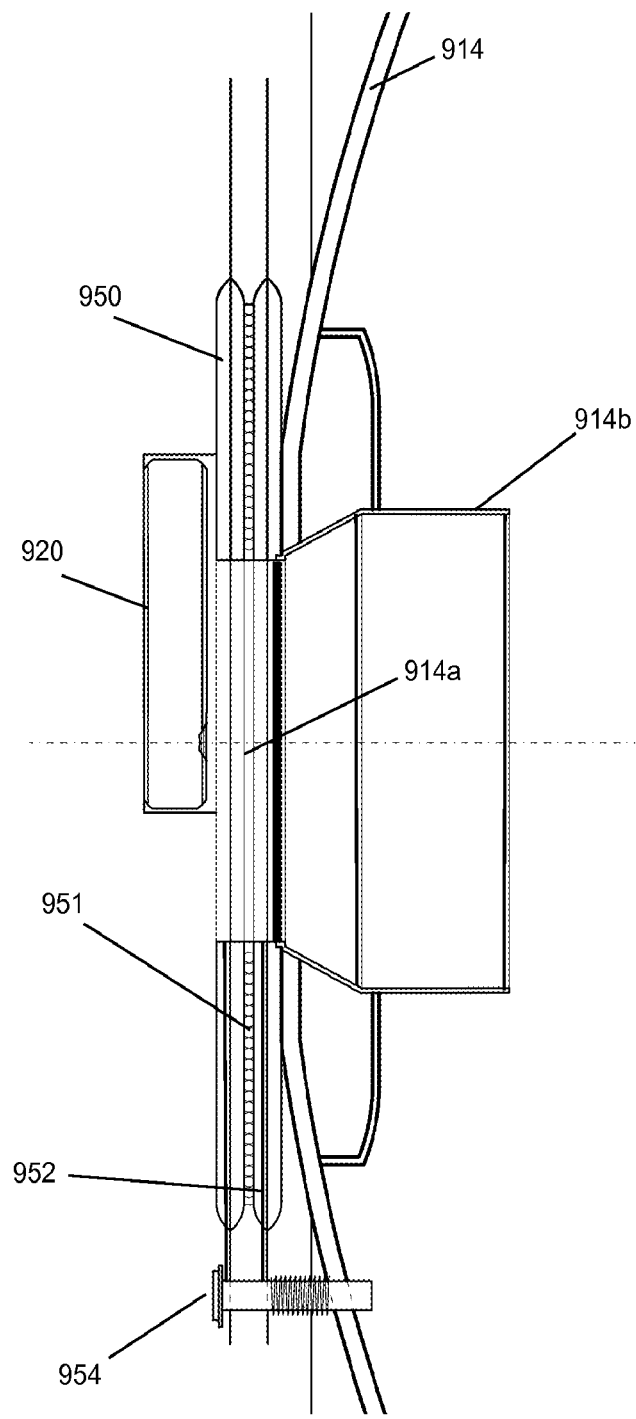
FIG. 9 depicts a side view of a mounting plate, according to an embodiment of the present invention.

According to an embodiment of the present invention, an aperture hood 714b, 814b, 914b (as shown in FIGS. 7, 8 and 9) may be used to prevent light from leaking into the image acquisition device 120 lens 120a. Light leak may cause images to look smoky or foggy. The aperture hood 714b, 814b, 914b (as shown in FIGS. 7, 8 and 9) may be connected to the inner surface of the reflector and aligned with the reflector aperture 714a. However, one having ordinary skill in the art will appreciate that size, shape and placement of the aperture hood 714b, 814b, 914b (as shown in FIGS. 7, 8 and 9) may be varied depending on the particular application.

According to an embodiment of the present invention, an optional vertical stand 116 may be used to support and stabilize the imaging apparatus 110. The vertical stand 116 may be connected to other horizontal supports 115, 117 which allow for the height or horizontal position of the imaging apparatus 110 to be adjusted. Wheels or castors of the type shown in FIG. 1 may also be connected to the bottom horizontal stand 115 so as to allow the entire apparatus to be easily rolled from one location to another. One having ordinary skill in the art will appreciate that other suitable stands such as a tripods or monopods may also be used to support the apparatus.

According to an embodiment of the present invention, the image acquisition device 120 comprises a still or video camera of the type commercially available in the market place. The image acquisition device 120 is generally configured so that the lens 120a of the imaging device 120 is in a plane parallel to the plane of the light source 112. In addition, the imaging apparatus may be configured so that the imaging device lens 120a, light source 112 and reflector 114 form concentric circles as illustrated. Generally, the image acquisition device 120 lens 120a will be centered within the opening of the aperture 114a.

According to an embodiment of the present invention, the image acquisition device 120 is a digital camera, however one having ordinary skill in the art will appreciate that a variety of suitable devices may be used for this purpose. In exemplary embodiments, the digital camera may be a stand-alone device such as an SLR or "point-and-shoot" camera or may be integrated into another device such as a smart phone (e.g., iPhone) or tablet computer.

According to an embodiment of the present invention, the imaging apparatus 110 may be removably connected to horizontal support 117 via a mounting point on reflector 114. In addition, the imaging apparatus 110 may be removed from the stand and supported directly by the operator for close-up shots or other shots that would be difficult to capture with the stand 115, 116, 117 connected.

Figure 2:
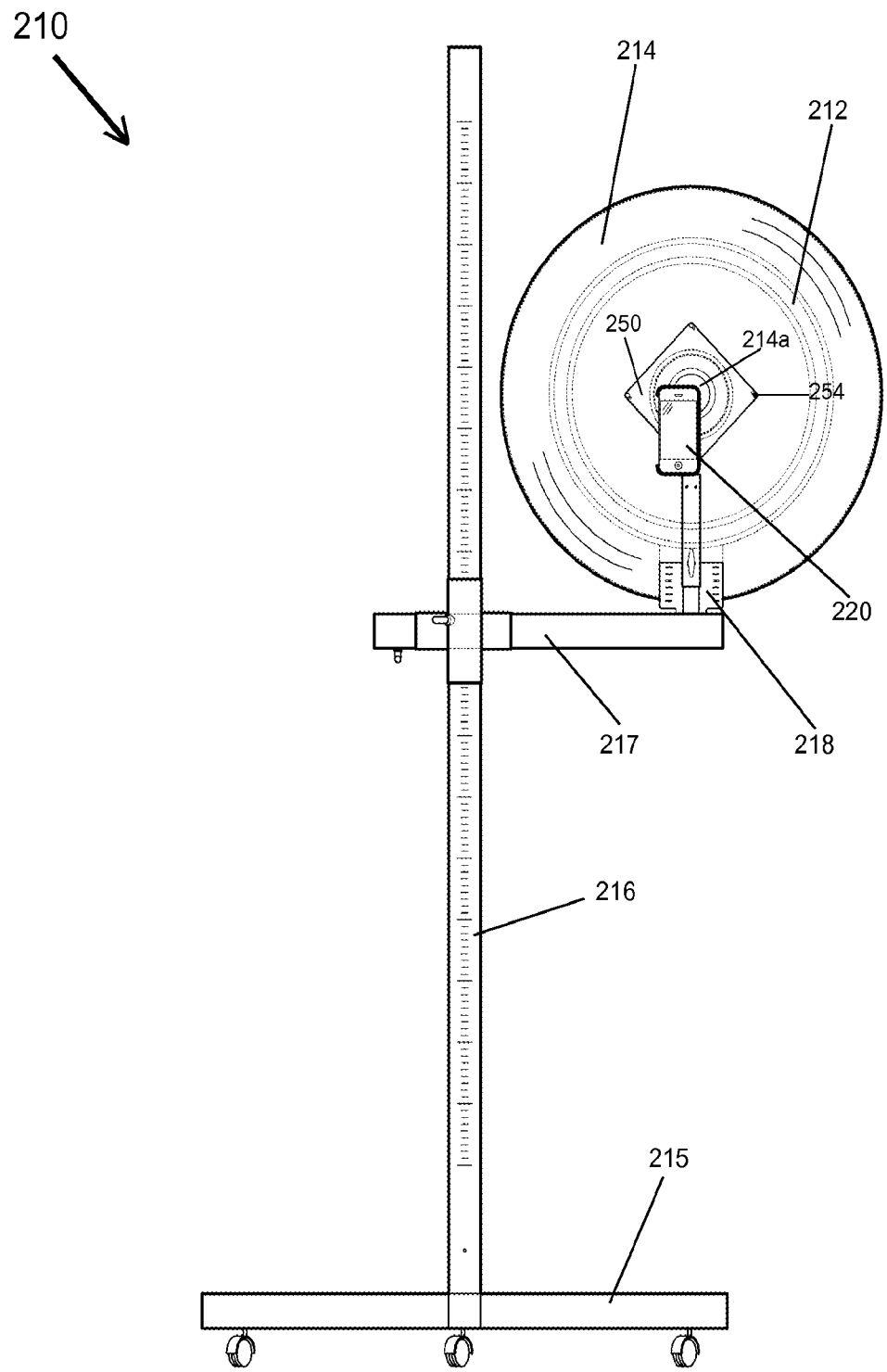
FIG. 2 depicts a rear view of an imaging apparatus, according to an embodiment of the present invention.

FIG. 2 shows a rear view of the imaging apparatus according to an embodiment of the present. This view illustrates how the image acquisition device 220 may be connected to the reflector 214 via a rotating plate apparatus 250. The image acquisition device may be connected to the rotating plate 250 through any suitable means and the rotating plate 250 is connected directly to the reflector 214. According to an embodiment of the present invention, the image acquisition device 220 comprises a smart phone with still and motion photography capabilities.

Figure 3:
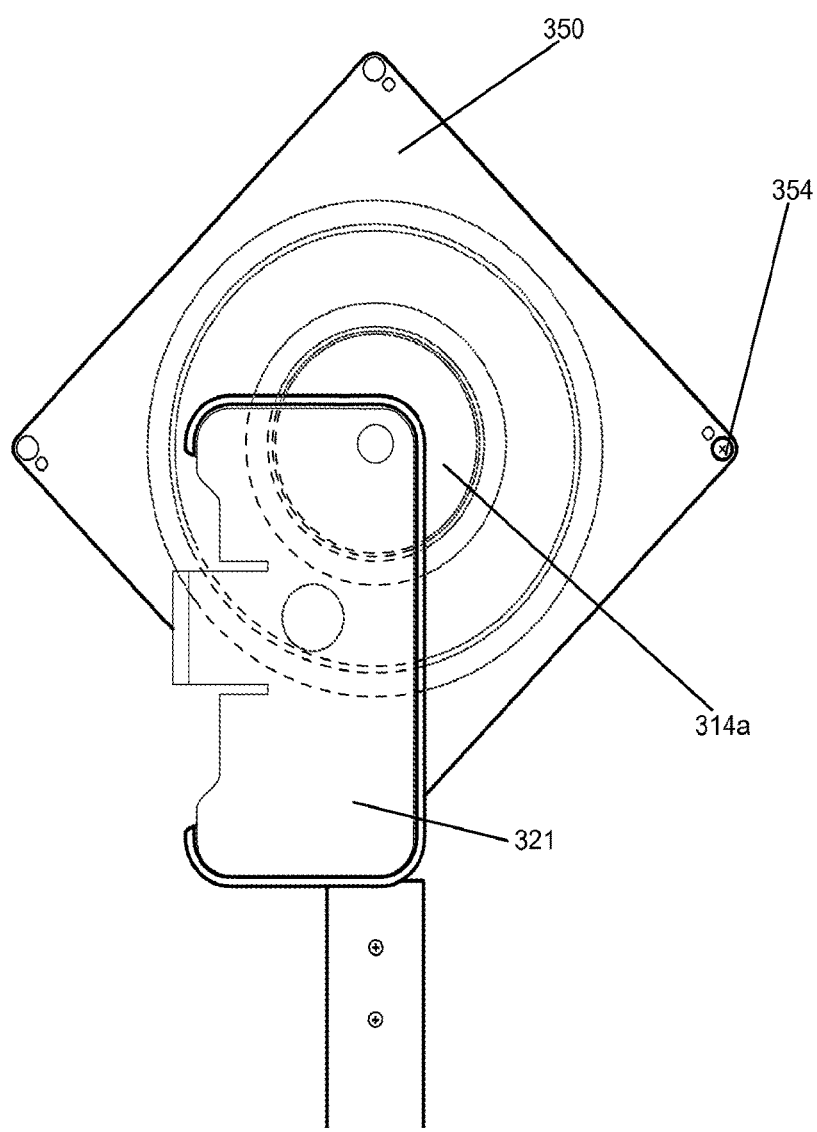
FIG. 3 depicts a rear view of an imaging apparatus, according to an embodiment of the present invention.

FIG. 3 illustrates a close-up view of the rotating plate 350 and image acquisition device mounting bracket 321 according to an embodiment of the present invention. The image acquisition device mounting bracket 321 may be configured to cradle specific acquisition devices such as smart phones or table computers. The acquisition device mounting bracket 321 may be configured so that the lens of the image acquisition device is centered in the reflector aperture. The image acquisition device mounting bracket 321 illustrated is configured specifically to cradle an Apple iPhone although one having ordinary skill in the art will appreciate that other mountain devices can be configured based on the type of image acquisition device used.

Figure 4:
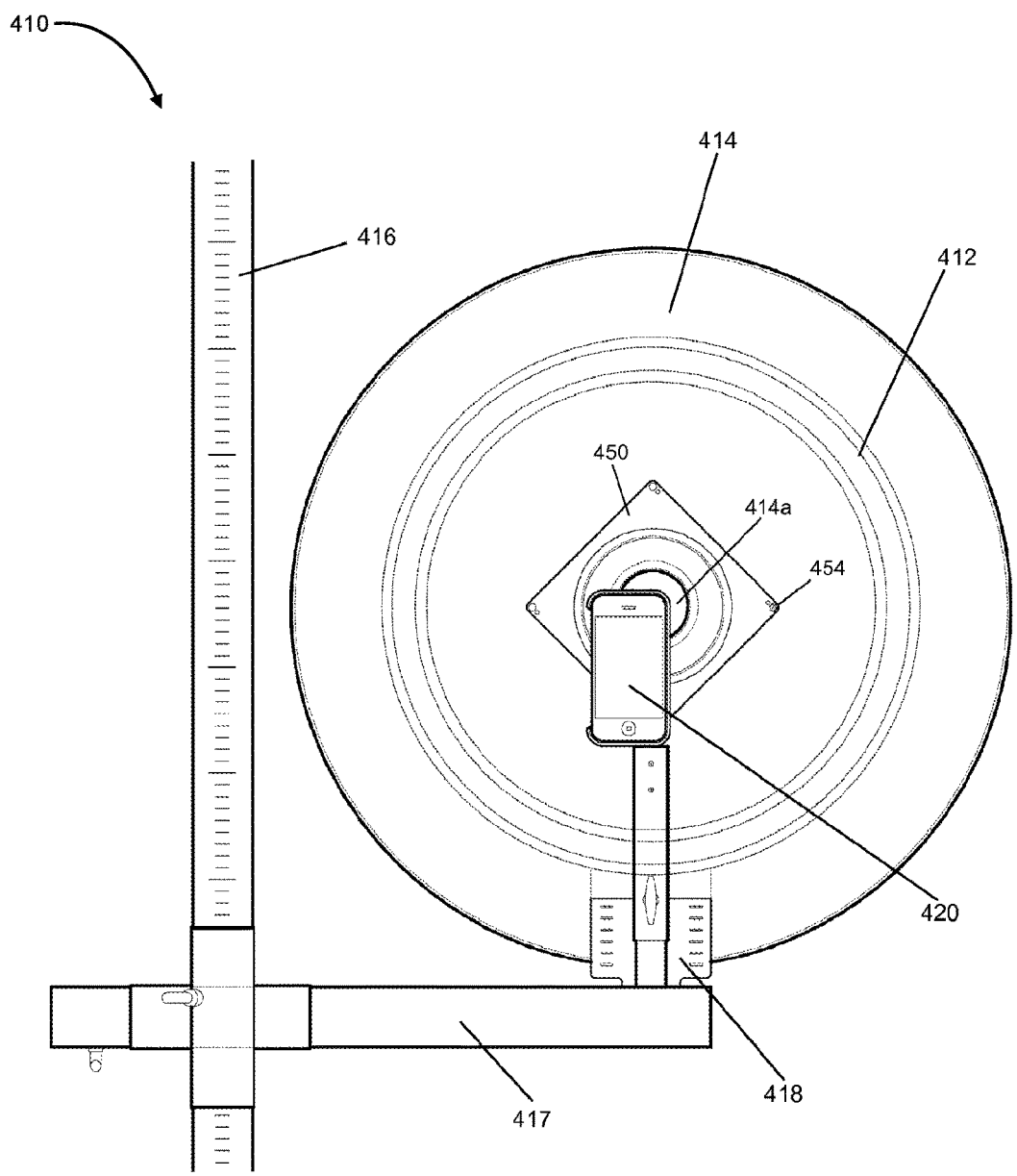
FIG. 4 depicts a rear view of an imaging apparatus, according to an embodiment of the present invention.
Figure 5:
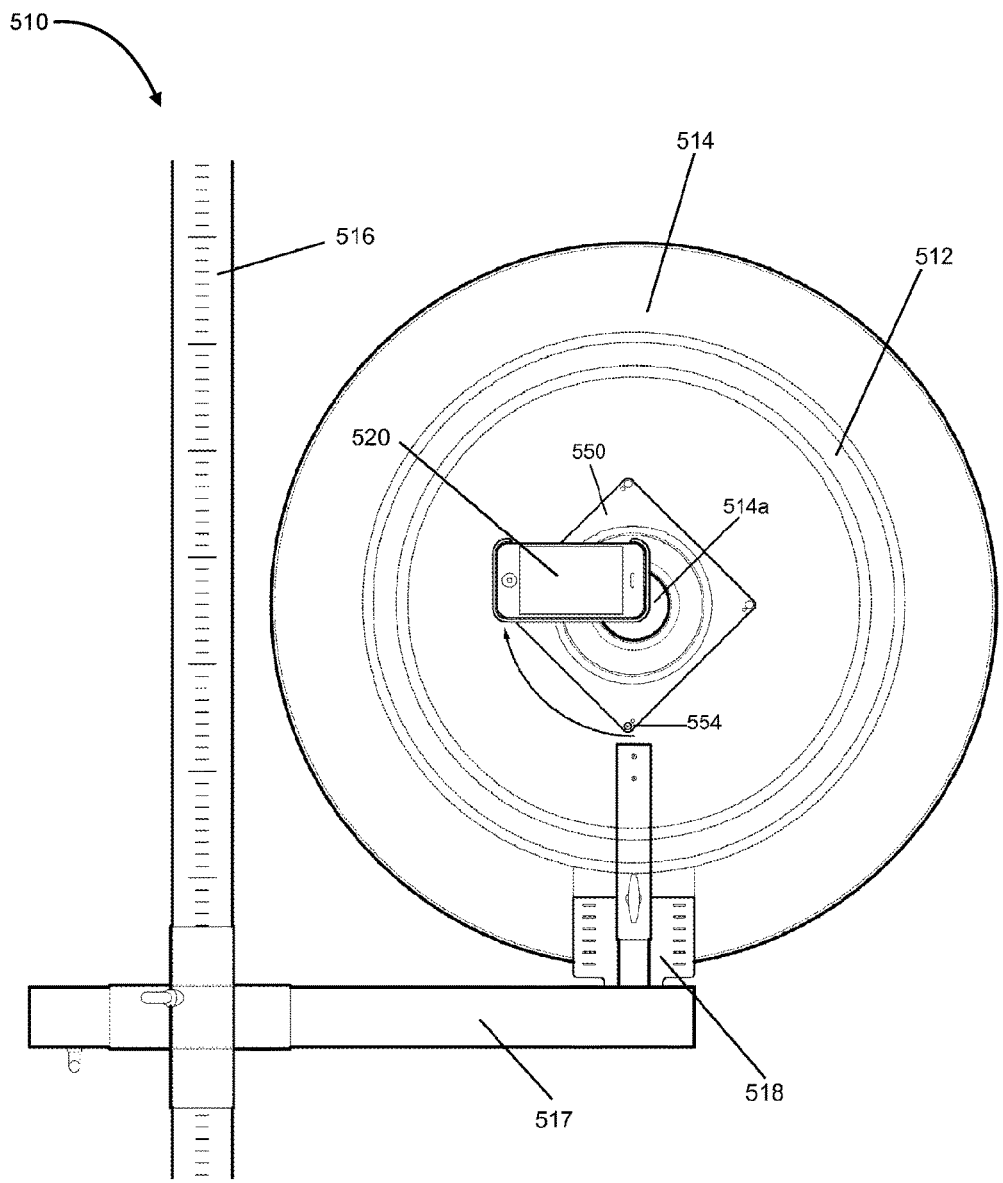
FIG. 5 depicts a rear view of an imaging apparatus, according to an embodiment of the present invention.

FIGS. 4 and 5 depict a rear view of the imaging apparatus according to an embodiment of the present invention. This embodiment allows the image acquisition device 420, 520 to be rotated ninety (90) degrees in the clockwise direction. This ability to rotate the image acquisition device 420, 520 allows the operator to easily switch from portrait to landscape view based on a particular image acquisition scheme. The rotating plate apparatus 450, 550 is configured to allow the image acquisition device 420, 520 to rotate about an axis of the image acquisition device's lens. In this way, the orientation of the image acquisition device 420, 520 lens in the horizontal and vertical axes remains constant through the rotation.

Figure 6:
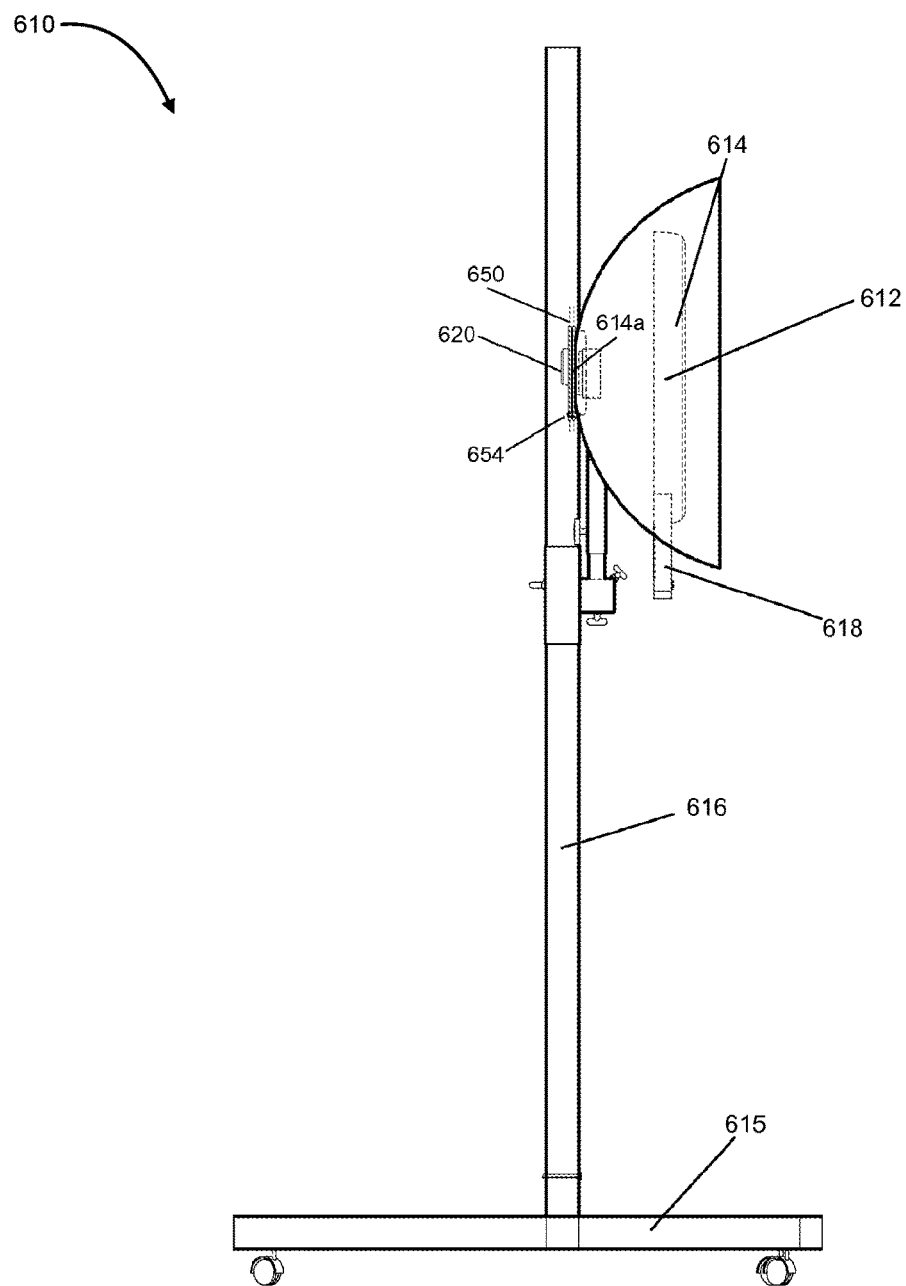
FIG. 6 depicts a side view of an imaging apparatus, according to an embodiment of the present invention.

FIG. 6 illustrates a side view of the image acquisition device 610 according to an embodiment of the present invention. The reflector 614 is bowl shaped but, as noted above, may be of any suitable size and shape. This view also illustrates that the mounting plate to which the image acquisition device 620 is connected comprises a rotating plate 650 and stationary plate 652. FIG. 7 illustrates a side cutaway view of the imaging apparatus 710 according to an embodiment of the present invention. The light source 712 is configured to generally aim light backwards into the inner surface of the reflector 714. In this configuration, light emitted by the light source 712 bounces off of the inner surface of the reflector and towards the subject. Exemplary light paths are shown as dashed lines in FIG. 7. The resulting light from this "bouncing" process is typically warmer and more evenly dispersed than direct light. Such bounced light may be useful in situations where even contrast and lighting are desired such external medical imaging, fashion photography or modeling. The light leaving the reflector 714 then bounces off of an object of interest where such light is reflected off of the object of interest and focused through the reflector 714 aperture 714a and into the lens of the image acquisition device. One having ordinary skill in the art will appreciate that the lighting apparatus disclosed herein can be used in variety of settings for both still and video photography.

FIGS. 7 and 8 also illustrate a side view of the image acquisition device 720, 820 rotation via the rotating plate apparatus according to an embodiment of the present invention. The image acquisition device 720 may initially start in the vertical position for capturing images in portrait view. The image acquisition device 820 may then be rotated ninety degrees in the clockwise direction for capturing images in landscape view.

FIG. 9 shows a close-up side view of how the image acquisition device 920 is connected to the reflector 914 via a rotating plate apparatus according to an embodiment of the present invention. Lower plate 952 is connected to the reflector 914 through any suitable means. A rotating upper plate 950 is connected to the lower plate 950 and a suitable bearing device 952 is connected between the plates. The bearing device 952 is configured to allow the upper plate 950 to rotate in a radial direction relative to the lower plate 952. During such rotation, the lower plate 952 remains stationary and only the upper plate 950 rotates. Rotation may be performed manually by the user or may be aided through the use of torsion springs. A lock pin 954 may be inserted through both plates so that they remain fixed relative to one another. The rotating plate shown in FIG. 9 is only one possible embodiment and one having ordinary skill in the art will appreciate that other rotating devices may be used for mounting the image acquisition device 920 to the reflector 914.

According to an embodiment of the present invention, the imaging apparatus described above may be integrated with an imaging system and utilize various image acquisition, storage and analysis methods. Such systems and methods can be used to carry out a "protocol" in which one or more corresponding sets of images of a subject are captured, preferably under substantially uniform and reproducible lighting conditions, and more preferably using an embodiment of the imaging apparatus as described above. In one embodiment, a protocol may include a plurality of image captures in which a subject is positioned in one or more pre-determined poses and the images are captured from one or more predetermined angles with respect to the subject. The protocol may also include a temporal aspect whereby images are captured at some initial time and then other images of the same subject are captured at some later time. This sort of protocol can allow for a comparison of the initial images with the later images to determine, for example, healing. One having ordinary skill in the art will appreciate that any suitable protocol can be defined.

For example, an exemplary breast analysis protocol could include left profile, right profile, front, and angled views of a subject's torso for both an "arms-raised" subject position and an "arms down" subject position. The captured images may be stored in a database and indexed based on a variety of parameters such as date, subject identification, provider, condition, etc. A protocol can also be self-determined or otherwise customized during the first performance thereof (e.g., during a first office visit or first home image capture), and then followed for one or more subsequent performances (e.g., during subsequent office visits or during subsequent home image captures).

The images can be captured using the imaging apparatus described above at a doctor's office or hospital, optionally with the assistance of a physician, assistant, or technician. The images can also be captured using the imaging apparatus described (or similar embodiment) above in a subject's home, or using a mobile device or tablet computer. The image acquisition process may also be implemented using a computer, mobile device or tablet. The stored images can later be retrieved from the database for any of a variety of purposes. For example, corresponding images taken in accord with a protocol on a plurality of different dates can be simultaneously display to facilitate comparative assessment by a user (e.g., a health care provider, a cosmetologist or other person) to aid in the assessment of disease state, healing, growth, or other bodily changes.

Figure 10:
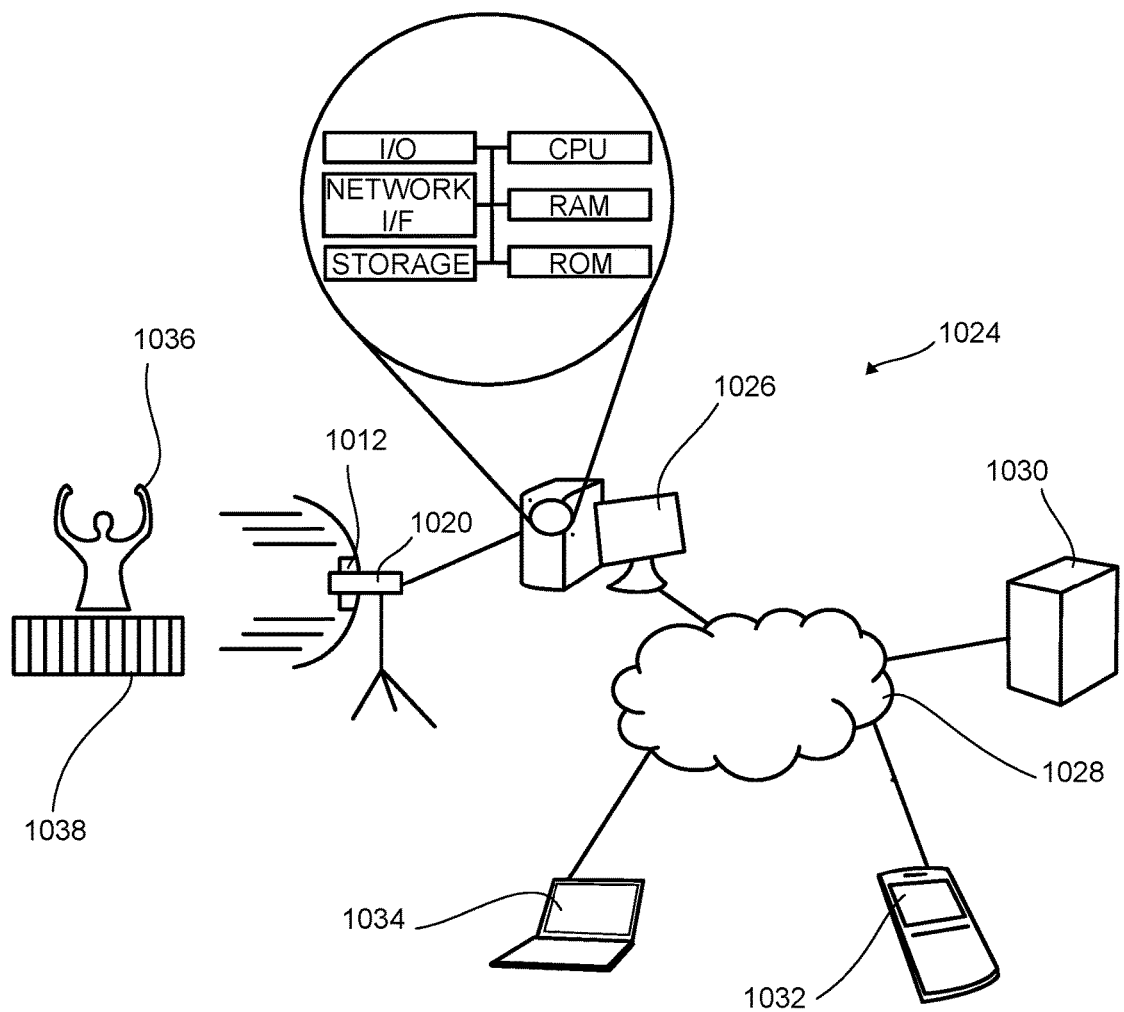
FIG. 10 depicts a network architecture of an image acquisition and analysis system, according to an embodiment of the present invention.

FIG. 10 illustrates a basic image acquisition and analysis system architecture according to an embodiment of the present invention. The system 1024 generally includes an imaging apparatus 1010 such as that described above. The imaging apparatus 1010 may be communicatively connected to a digital data processing module 1026, which is in turn communicatively connected via a network 1028 to a database module 1030 which can store subject data, captured images, and/or any other data acquired or used by the system 1024. According to an embodiment of the present invention, the database module 1030 is communicatively connected to the digital data processing module 1026 via a network 1028, but the database module 1030 can be communicatively connected to the digital data processing module 1026 via direct connection, or the database module 1030 or can be formed integrally within the digital data processing module 1026 (e.g., as files stored on a hard drive or memory card of the digital data processing module 1026).

According to an embodiment of the present invention, the digital data processing module 1026 can be any of a variety of conventional devices known in the art, including desktop computers, workstations, minicomputers, laptop computers, tablet computers, PDAs, cell phones, or other digital data processing modules of the type that are commercially available in the marketplace and that are suitable for operation in the illustrated system as described herein, all as adapted in accord with the teachings hereof.

According to an embodiment of the present invention, the digital data processing module 1026 and the database module 1030 can also be communicatively connected via the network 1028 with a variety of other digital data processing systems 1032, 1034. The network 1028 can be any of the Internet, a wide area network (WAN), a metropolitan area network (MAN), a local area network (LAN), a telephone network, cellular data network (e.g., 3G, 4G) and/or a combination of these and other networks (wired, wireless, public, private or otherwise).

According to an embodiment of the present invention, the digital data processing module 1026 comprises a central processing unit, memory, storage and input/output units and other constituent components (not shown) of the type conventional in the art that are configured to execute applications (e.g., software suitable for displaying user interfaces, said interfaces optionally being generated by a remote server, interfacing with the database module 1030, and managing and/or performing capture, transmission, storage, analysis, display, and/or other processing of subject data and/or images.

According to an embodiment of the present invention, the digital data processing module 1026 includes a web browser of the type commercially available in the marketplace and operative for, by way of example, retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HTTP requests with respect to those pages/streams or otherwise (e.g., for submitting to a server information from the completed input fields), and so forth. The web pages or other markup language can be in HTML, Ruby on Rails or other conventional forms, including embedded XML, scripts, controls, and so forth as adapted in accord with the teachings hereof.

While the forgoing functions attributed to the digital data processing module 1026 are described here in the context of web pages, one having ordinary skill in the art will appreciate that one or more of the foregoing functions may be performed on the digital data processing module 1026 other than by "web browser" software.

The central processing, memory, storage, and input/output units of the digital data processing module 1026 may be configured to form and/or may be supplemented by other elements of the type known in the art desirable or necessary to support operation of the system 1024. These can include, by way of non-limiting example, peripheral devices (such as keyboards and monitors), operating systems, database management systems, mySQL databases and network interface cards and software, e.g., for supporting communications with other data processing devices over the network 1028.

According to an embodiment of the present invention, the digital data processing module 1026 and the imaging apparatus 1010 communicatively connected thereto can be situated in a physician's office. The imaging apparatus 1010 can be used to capture images of a subject 1036 and a color chart 1038 (e.g., a Pantone screen) with uniform and reproducible light parameters. For example, a protocol can be defined based on certain parameters (e.g., subject poses, sequence of subject poses, light parameters, subject-camera distance, color chart size, focal length of imaging device, etc.). The physician or a physician's assistant can carry out the protocol during an office visit, capturing one or more images of the subject 1036. These captured images can then be transmitted to and/or stored in the database module 1030 for subsequent retrieval, review, comparison, and/or long-term storage. In alternative embodiments, the digital data processing module 1036 can be situated at a subject's home, at a commercial establishment, and/or as a mobile device and can be operated, for example, by a subject 1036, or an associate of the subject 1036 such as a spouse, friend or relative.

Figure 11:
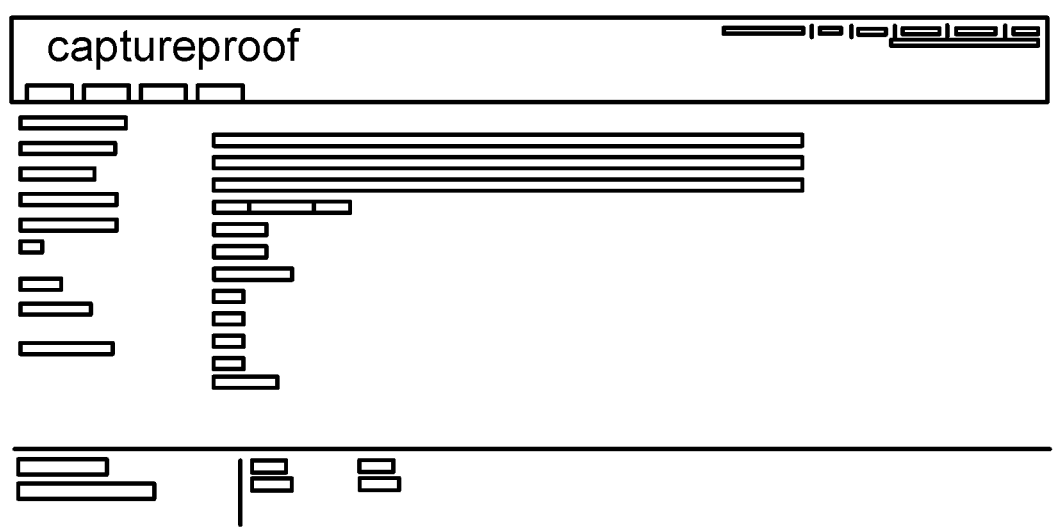
FIG. 11 depicts a new subject entry form, according to an embodiment of the present invention.

According to an embodiment of the present invention, execution of various protocols can be facilitated by a software user interface executed on the digital data processing module 1026. The interface can be in the form of a stand-alone executable program, or can be implemented as a series of web pages served over the network 1028 from a server communicatively connected to the database module 1030. According to an embodiment of the present invention, the software user interface can allow creation of a new subject record, for example using a web page as shown in FIG. 11, in which data relating to a particular subject such as subject number, subject enrollment date, sex, date of birth, doctor, etc. can be entered. The software user interface can also permit entry of various data relating to a study, such as the study name and the company name.

Figure 12:
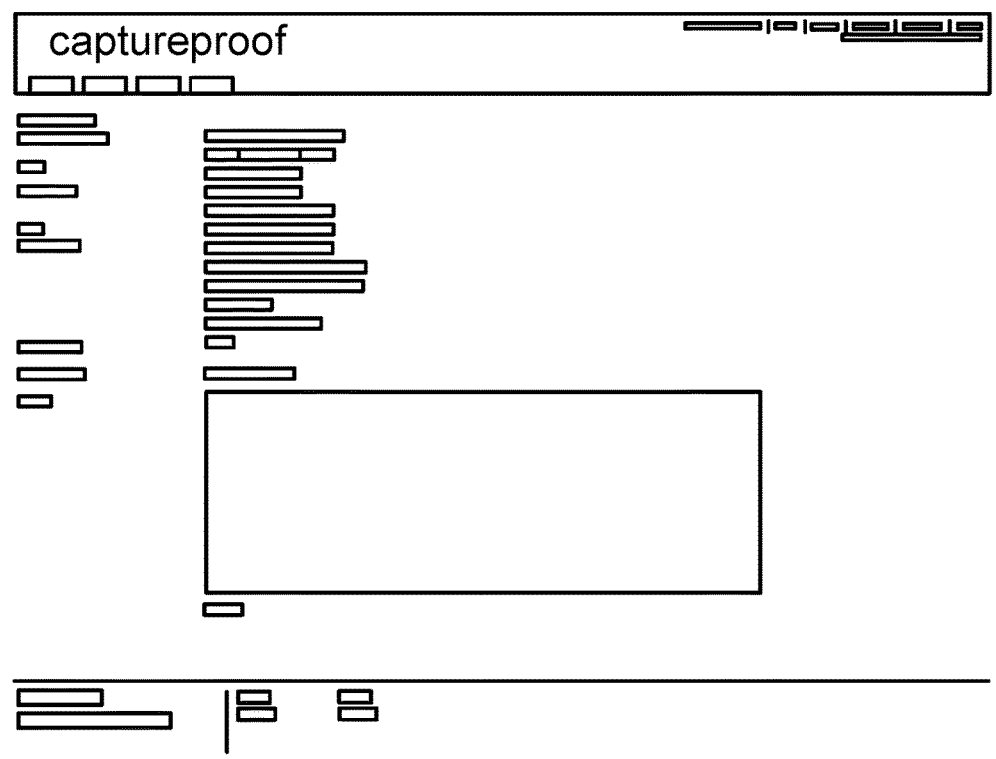
FIG. 12 depicts a new visit entry form, according to an embodiment of the present invention.

According to an embodiment of the present invention, the software user interface can also permit assignment of newly captured images to a preexisting subject record, for example as shown in FIG. 12. As shown, a preexisting subject record can be selected (e.g., by subject number). Images can then be assigned to that subject number with a variety of additional data, such as date of image capture, type of procedure being documented (e.g., an augmentation or a reconstruction), and a visit type/sequence (e.g., 12 month follow-up, 18 month follow-up, baseline, other, etc.).

Figure 13:
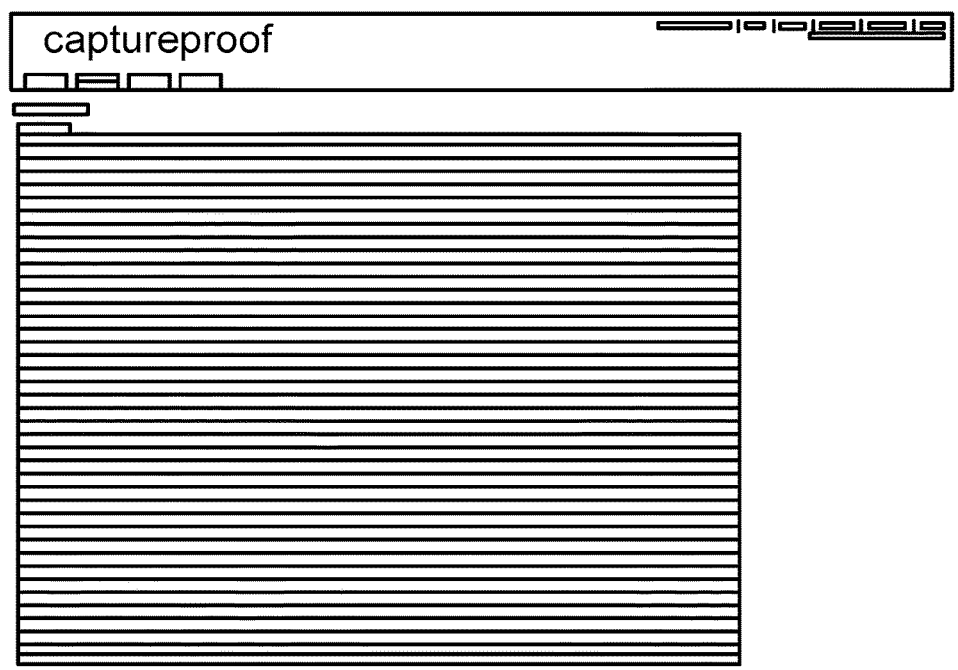
FIG. 13 depicts a database indexed by subject number, according to an embodiment of the present invention.

According to an embodiment of the present invention, as shown in FIG. 13, the software interface can also include provisions for managing a database of subject records, which can optionally be stored in the database module 1030 (as shown in FIG. 10). An authorized user can select from a plurality of subject records stored in the database module 1030 to view, edit, analyze and/or delete the record.

Figure 14:
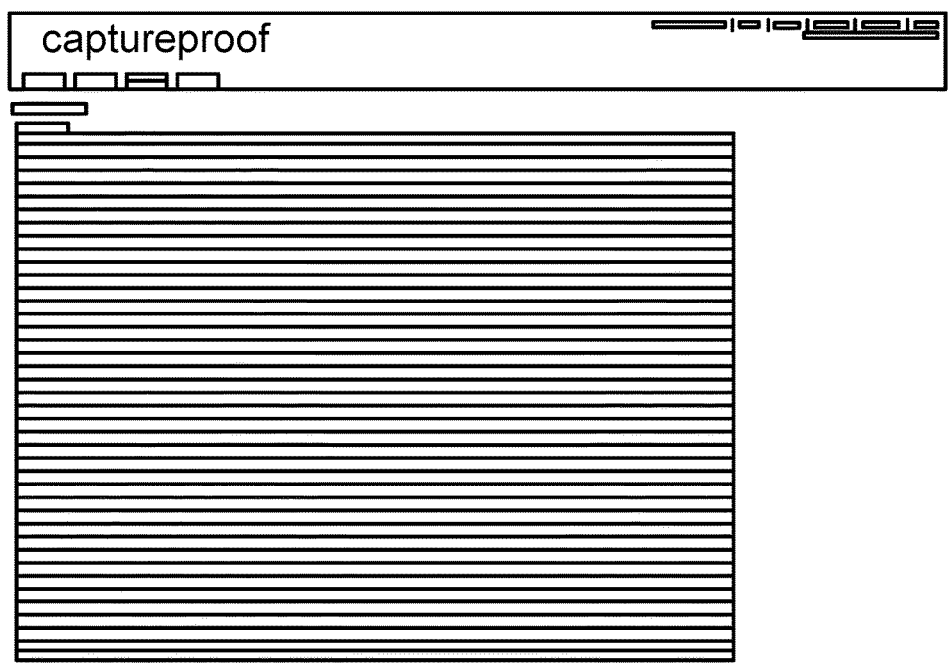
FIG. 14 depicts a database indexed by visit number, according to an embodiment of the present invention.
Figure 15:
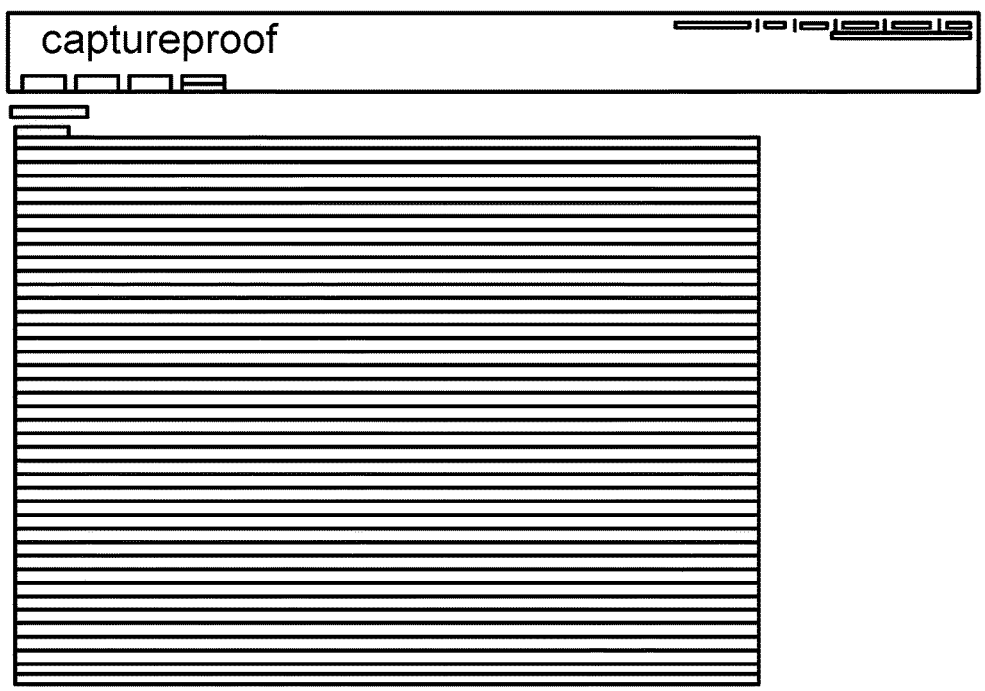
FIG. 15 depicts a database indexed by capture number, according to an embodiment of the present invention.

According to an embodiment of the present invention, as shown in FIG. 14, the database contents can also be indexed by visit number such that a user can view, edit, analyze, and/or delete one or more records corresponding to particular subject's visits. Additionally, as shown in FIG. 15, the database contents can also be indexed by specific image captures such that a user can view, edit, analyze, or delete one or more records corresponding to particular image captures.

Figure 16:
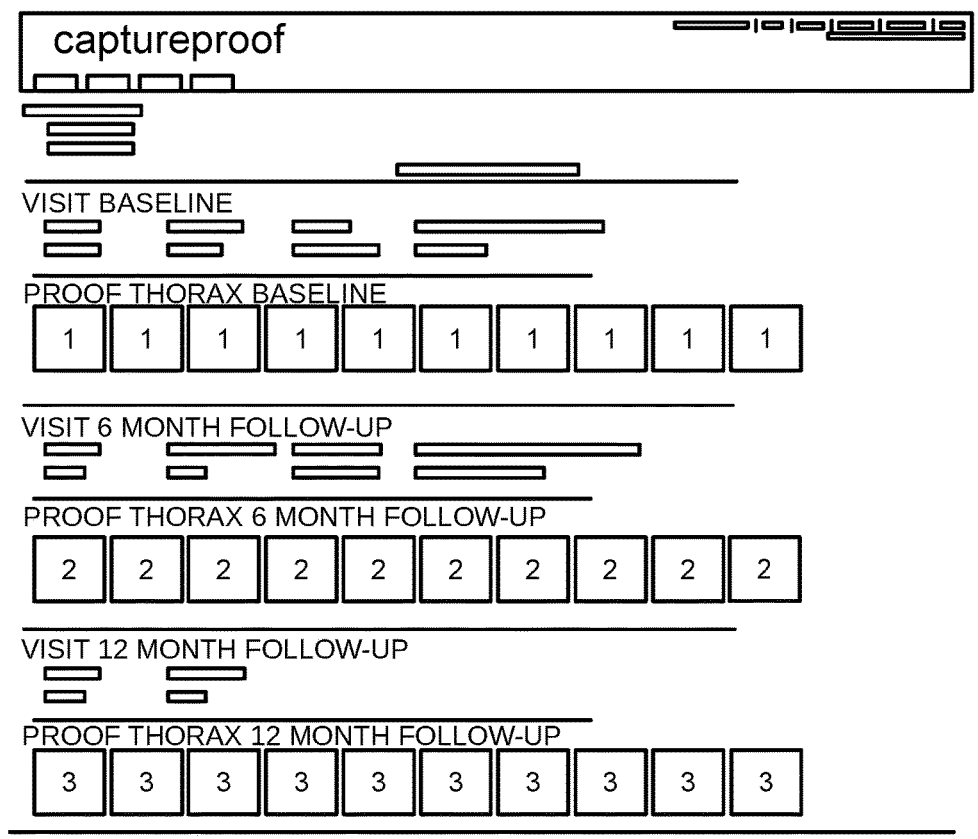
FIG. 16 depicts a subject history page, according to an embodiment of the present invention.

According to an embodiment of the present invention, as shown in FIG. 16, a subject record can be accessed by a user, using the software user interface, to display subject data and subject images for a particular subject. In the illustrated embodiment, a plurality of thorax image protocols are displayed, each captured on a different date but under substantially uniform lighting, equipment, camera height and distance conditions. Each protocol also includes the same views of the subject (e.g., left profile, right profile, front, angle 1, and angle 2 all with arms up and down, respectively). Thus, a user can quickly compare views of the subject with substantially uniform light, subject-camera distance, and subject position, across multiple dates that may or may not be temporally proximate. For example, a user can simultaneously or sequentially view baseline, 6 month follow-up, and 12 month follow-up left profile images of the same subject under substantially the same lighting conditions and image parameters.

Figure 17:
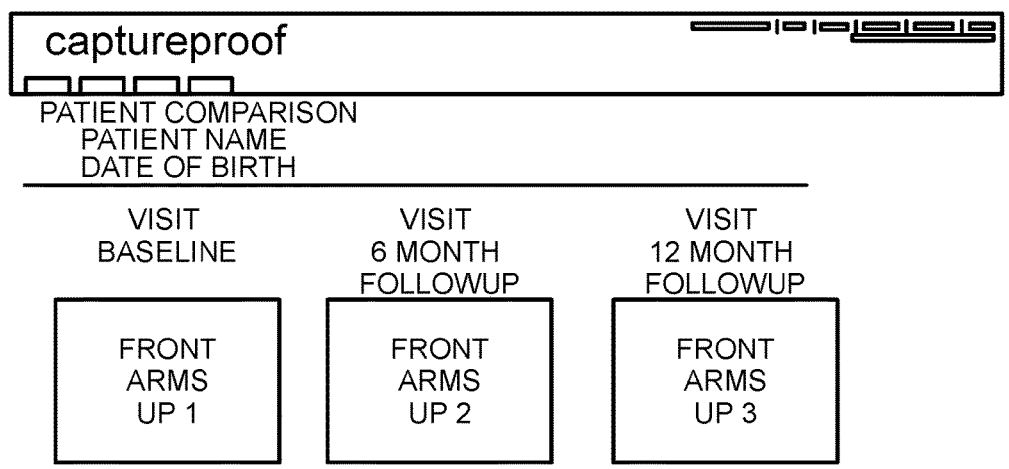
FIG. 17 depicts a subject comparison page, according to an embodiment of the present invention.

According to an embodiment of the present invention, as shown in FIG. 17, a particular view can be selected and the images from each protocol corresponding to that view can be displayed side-by-side for comparison. One having ordinary skill in the art will appreciate that the system can allow a user to make diagnoses, assess healing or growth, assess beauty characteristics, or perform one or more analyses on the captured image data. This can also allow the user to view any combination of before and after images, provided that the images being compared were taken at different times. In addition, embodiments of the present invention allow for "post production" filtering to be applied to images to aid in the analysis. By way of example and not limitation, certain color filters may be applied to the resulting images to enhance contrast or help isolate certain features that are difficult to view. One having ordinary skill in the art will appreciate the nature and types of image manipulation that may be performed to aid image analysis.

Figure 18:
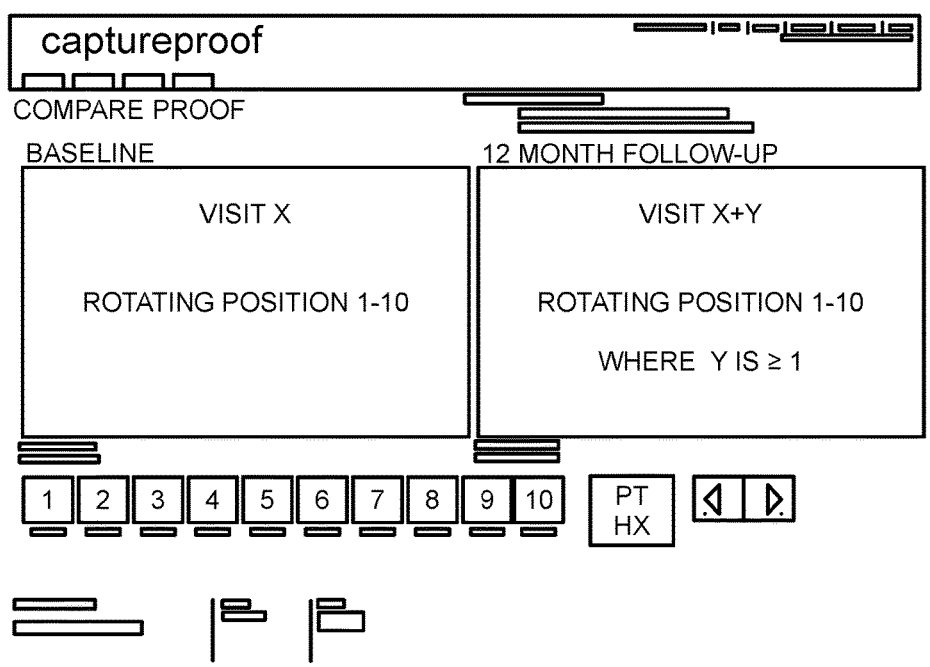
FIG. 18 depicts a subject comparison page, according to an embodiment of the present invention.

According to an embodiment of the present invention, FIG. 18 illustrates a system view that permits comparative organization and/or viewing of captured images. As shown, the interface can include a page in which the user is presented with two or more comparison panes in which captured images can be displayed. The comparison panes can be used to display, for example, a first image of a particular subject taken in accord with a protocol on a first date (e.g., during a first office visit) side-by-side with a corresponding image of the same subject taken in accord with the protocol on a second date (e.g., during a follow-up office visit). The corresponding images can be, for example, the same "indexed" position (e.g., the same subject position) from the protocol.

The user can select which images to display for comparison by selecting from one or more protocols and from one or more positions that define the selected protocol. In the illustrated embodiment, "baseline" is chosen from a pull-down menu corresponding to the left display pane and "12 month follow-up" is chosen from a pull-down menu corresponding to the right display pane. Thus, the images displayed in the left and right are selected from the images captured during the subject's baseline visit and during the subject's 12 month follow-up visit, respectively.

Thumbnail images corresponding to each component (e.g., each subject position) of the selected protocol can also be displayed to the user, for example in a line below the comparison panes. Such a view allows the user to select a thumbnail image corresponding to a particular subject position to cause the interface to display the images from each of the selected protocols corresponding to that subject position in the comparison panes. In other words, a user can select the "position 4" thumbnail to cause a full-size image of the subject placed in position 4 taken during the subject's baseline visit to be displayed adjacent to a full-size image of the subject placed in position 4 taken during the subject's 12 month follow-up visit. It will be appreciated that the interface can permit a user to easily view, compare, and switch between before and after images of the same subject in the substantially the same position.

According to an embodiment of the present invention, and referring to FIG. 10, the digital data processing module 1026 can also be configured to perform any of a variety of image processing operations on the captured images, such as color correction and normalization based on the color chart 1038, which can optionally be captured in each of the images. The digital data processing module 1026 can also perform image comparison operations on the captured images, flagging potential variations for visual review by a user. For example, in one embodiment, the digital data processing module 1026 can be configured to perform a volumetric analysis of a subject's breast based on captured image data, and compare that analysis to data derived from other captured images of the same subject on different dates. When a discrepancy is noted that exceeds a predetermined threshold value, an alert can be provided to the user via the software interface.

Potential users of the digital data processing module 1026 include institutions (e.g., research organizations, hospitals, and/or universities), which can be referenced by a variety of parameters such as institution name, address, phone, and institution study name. Users of the system 1024 can also include corporations (e.g., pharmaceutical companies, medical device manufacturers), which can be referenced by corporation name, address, phone, and corporation study name. Data acquired and manipulated by the digital data processing module 1026 can also be indexed based on clinical trial, for example by tagging with data such as trial name, trial description, and trial status.

According to an embodiment of the present invention, the digital data processing module 1026 can also include various security features, such as requiring a username and password, to preserve subject confidentiality and comply with privacy laws. In one embodiment, subject 1036 name data, visitation data, clinical data, proofs, and/or subject images can each be stored in separate, secured database modules 1030. The system 1024 can also be adapted to log the IP addresses of all users that access the system 1024, along with a date and time that the system was accessed. The system 1024 can also be configured to prevent a user from storing or reproducing captured images in an unauthorized manner. For example, the digital data processing module 1026 can be configured to disable personal e-mail, screen capture functions (to the extent possible), removable storage devices, etc.

According to an embodiment of the present invention, the various features of the digital data processing module 1026 can be selectively activated and deactivated based on the role of a particular user or group of users. Thus, certain features may be available to some users but not to others. Exemplary user roles include admin, corporate, doctor, subject, technician, etc. Feature access can also be determined individually on a user-by-user basis. In one embodiment, doctors that are not part of a particular clinical trial cannot access subject or image data associated with that trial.

According to an embodiment of the present invention, the system 1024 can also include a database of physicians which can be used to assign a particular physician to a particular subject or image capture. Physician data that can be stored by the system 1024 may include name, address, phone, website, fax, email, license number, and specialty (e.g., dermatology, emergency medicine, oncology, etc.)

According to an embodiment of the present invention, the software interface can also include a multi-field database search capability for searching the database module 1030 based on fields such as country, camera code, institution, doctor, subject, date range, diagnosis, treatment, protocol, sex, specialty, etc. A reporting tool can also be provided to generate reports (e.g., periodic usage reports, subject reports, etc.).

Figure 19:
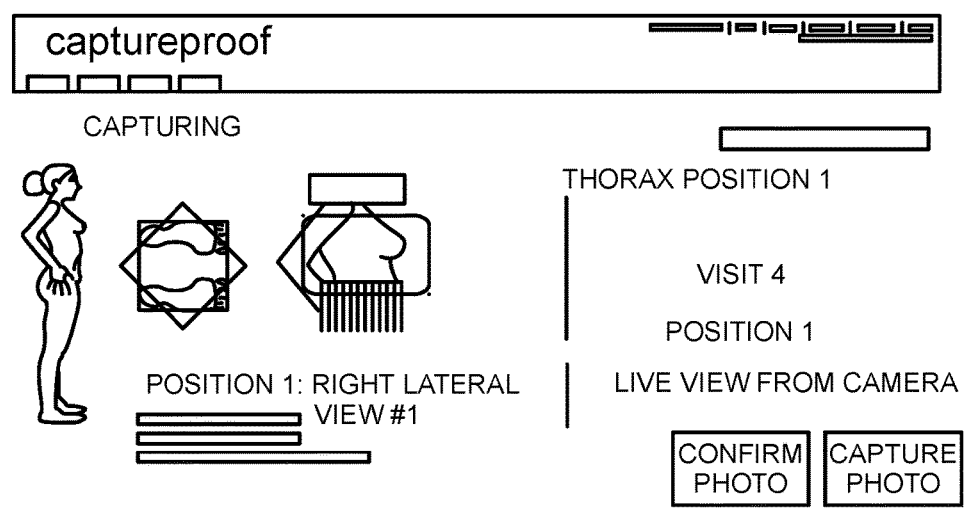
FIG. 19 depicts a protocol instruction page, according to an embodiment of the present invention.

According to an embodiment of the present invention, when capturing a new proof (e.g., a subject image), the software interface's display can be split into two sections (e.g., right and left). For new subjects, the left side of the screen can display instructions for capturing the correct image as well as an image showing the ideal camera position on an animated character (as shown in FIG. 19). If the selected protocol requires more than one image capture, the instructions and animation can change for each. For returning subjects, the left side of the screen can show the identical image captured during the subject's baseline visit. For example, if this is the subject's third visit, the baseline image (the images taken during the subject's first visit) can be displayed. The displayed baseline image can change as the protocol is carried out such that it constantly corresponds to the image being captured. For example, if ten pictures are required for a particular protocol and the fourth image is being captured, the left side of the screen can show the fourth image of the baseline visit.

According to an embodiment of the present invention, the software may be configured to show a live camera feed on the right side of the screen that can be controlled from the interface (e.g., moved up, down, left, right, zoomed, etc.). Depending on the protocol selected, the camera can begin in a default position/zoom. Before the user begins capturing images for each protocol, they can first take a picture of the background (no subject, no color chart) which can be used to set the white balance. Much like the subject image captures, there will be instructions to take this first "white balance" image on the left side of the screen. After this image, the protocol can begin.

When capturing each image (active live feed), a button can appear below the live feed which reads "Capture Proof." When selected, the camera will capture the presently observed scene and store it as an image file on a storage medium of the digital data processing module 1026 (e.g., RAM, a hard drive, a removable disk, or an attached database system). After capturing each image, two new buttons can appear below the live feed which read "Confirm Proof" and "Retake Proof" Upon clicking the "Confirm Proof" button, the user proceeds to the next image capture. Upon clicking the "Retake Proof" button, the user is able to retake the previous image.

When a user scrolls over a captured image, a loupe effect is available in which the user can selectively view an enlarged version of a specified area of the captured image. In addition, the loupe effect can be configured to allow a user to simultaneously enlarge similar portions of two images while those images are side by side, thus allowing a more detailed comparison. Various mirroring, morphing, highlighting, volumetric, and drawing tools can also be included in the interface software.

According to an embodiment of the present invention, the interface can also include a "Request Slide" button displayed in connection with a captured image. When selected by a user, the user can be prompted to label the image as a "print" or as a "projection" and to assign a subject visit date to the image (e.g., baseline or 6-month follow-up). The user can then be prompted to select from one or more captured images to be used for the slide. Thumbnails of all positions under the current protocol (e.g., Picture 1 of 8, 2 of 8, etc.) can be displayed in a row across the bottom of a list box. Multiple thumbnails can be selected and, when a thumbnail is selected, it can be highlighted. When the user is finished entering data and selecting images, a completed slide request can be issued.

After a request for slides/projections has been submitted, the request will be received by a "back-end user" via an e-mail or other system notification which can contain data such as a slide request number, a subject name, a front-end user name who requested the slide/projection, etc. The requests can appear in a line-item list containing the slide request number, a username, a subject name, a status, and an approve/deny status. Upon clicking an "approve" hyperlink, a password protected document will be available to be opened on the requesting front-end user's request history screen. An e-mail is also sent to the requesting user which contains the slide request number and the password to unlock the password-protected document. Upon clicking a "deny" hyperlink, a free text field will appear to the right of the hyperlink with a "cancel" and "send" button underneath it. Upon clicking the "Send" button, the content in the free text field is sent via email to the requesting front-end user.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

What is claimed is:

1. A method comprising:
    providing a plurality of protocol, the plurality of protocol including an individual protocol as a guide to acquire external visual images, the individual protocol specifying a posture, a position, a pose, a movement, a lighting, a time, a body part, a distance, or a combination thereof;
    acquiring the external visual images based on the individual protocol;
    storing the external visual images;
    displaying the plurality of protocol as a selection tool for displaying the external visual images;

detecting a selection of the individual protocol; and
displaying the external visual images acquired with the individual protocol based on the individual protocol being selected.

2. The method of claim 1 wherein displaying the external visual images acquired with the individual protocol includes displaying the external visual images in a comparative view.

3. The method of claim 1 further comprising generating an alert when the external visual images contain a discrepancy exceeding a predetermined threshold.

4. The method of claim 1 wherein displaying the plurality of protocol includes providing images displaying the plurality of protocol.

5. The method of claim 2 wherein displaying the external visual images includes displaying the external visual images based on the time of acquisition.

6. The method of claim 2 further comprising creating a loupe effect, a highlighting effect, a filtering effect, or a combination thereof simultaneously on similar portions of the external visual images.

7. The method of claim 1 wherein providing the plurality of protocol includes providing the individual protocol as instructions, animations, or images in a comparative fashion with respect to one of the external visual images.

8. A non-transitory computer readable medium, useful in association with a processor, including instructions configured to:
provide a plurality of protocol, the plurality of protocol including an individual protocol as a guide to acquire external visual images, the individual protocol specifying a posture, a position, a pose, a movement, a lighting, a time, a body part, a distance, or a combination thereof;
acquire the external visual images based on the individual protocol;
store the external visual images;
display the plurality of protocol as a selection tool for displaying the external visual images;
detect a selection of the individual protocol; and
display the external visual images acquired with the individual protocol based on the individual protocol being selected.

9. The non-transitory computer readable medium of claim 8, wherein the instructions configured to display the external visual images acquired with the individual protocol includes the instructions configured to display the external visual images in a comparative view.

10. The non-transitory computer readable medium of claim 8, further comprising instructions configured to generate an alert when the external visual images contain a discrepancy exceeding a predetermined threshold.

11. The non-transitory computer readable medium of claim 8, wherein the instructions configured to display the plurality of protocol include instructions configured to provide images displaying the plurality of protocol.

12. The non-transitory computer readable medium of claim 9, wherein the instructions configured to display the external visual images includes the instructions configured to display the external visual images based on the time of acquisition.

13. The non-transitory computer readable medium of claim 9, further comprising instructions configured to create a loupe effect, a highlighting effect, a filtering effect, or a combination thereof simultaneously on similar portions of the external visual images.

14. The non-transitory computer readable medium of claim 8, wherein the instructions configured to provide the plurality of protocol includes instructions configured to provide the individual protocol as instructions, animations, or images in a comparative fashion with respect to one of the external visual images.

15. A system comprising:
an interface configured to provide a plurality of protocol, the plurality of protocol including an individual protocol as a guide to acquire an external visual images, the individual protocol specifying a posture, a position, a pose, a movement, a lighting, a time, a body part, a distance, or a combination thereof, the interface configured to display the plurality of protocol as a selection tool for displaying the external visual images, and the interface configured to display the external visual images acquired with the individual protocol based on the individual protocol being selected; and
a digital data processing module, coupled to the display, configured to acquire the external visual images based on the individual protocol, store the external visual images, and the digital data processing module configured to detect a selection of the individual protocol.

16. The system of claim 15 wherein the display is configured to display the external visual images acquired with the individual protocol in a comparative view.

17. The system of claim 15 wherein the digital data processing module is configured to generate an alert when the external visual images contain a discrepancy exceeding a predetermined threshold.

18. The system of claim 15, wherein the display is configured to provide images displaying the plurality of protocol.

19. The system of claim 16 wherein the display is configured to display the external visual images based on the time of acquisition.

20. The system of claim 16 wherein the display is configured to create a loupe effect, a highlighting effect, a filtering effect, or a combination thereof simultaneously on similar portions of the external visual images.

21. The system of claim 15 wherein the display is configured to provide the individual protocol as instructions, animations, or images in a comparative fashion with respect to one of the external visual images.

* * * * *